United States Patent [19]

Scudder et al.

[11] Patent Number: 5,043,273
[45] Date of Patent: Aug. 27, 1991

[54] PHOSPHORYLATED GLYCOSIDASE INHIBITOR PRODRUGS

[75] Inventors: Peter R. Scudder; Raymond A. Dwek; Thomas W. Rademacher; Gary S. Jacob, all of Oxford, United Kingdom

[73] Assignee: Monsanto Company, St. Louis, Mo.

[21] Appl. No.: 394,914

[22] Filed: Aug. 17, 1989

[51] Int. Cl.$^5$ ............... C12P 9/00; C07P 207/40; C12N 9/12; C12N 9/16
[52] U.S. Cl. ............ 435/131; 435/193; 435/194; 435/196; 435/255; 514/329; 514/315; 548/526
[58] Field of Search ............ 435/131, 194, 255; 514/329, 315; 548/526

[56] References Cited

U.S. PATENT DOCUMENTS

| | | | |
|---|---|---|---|
| 4,065,562 | 12/1977 | Ohata et al. | 424/267 |
| 4,182,767 | 1/1980 | Murai et al. | 424/267 |
| 4,847,244 | 7/1989 | Rideout et al. | 514/50 |
| 4,849,430 | 7/1989 | Fleet et al. | 514/315 |

OTHER PUBLICATIONS

Fleet et al., Febs Lett. 237, 128-132 (1988).
Karpas et al., Proc. Natl. Acad. Sci. U.S.A. 85, 9229-9233 (1988).
Drueckhammer and Wong, J. Org. Chem. 50, 5912-5913 (1985).
Al-Nakib et al., J. Antimicrobiol, Chemother. 20, 887-892 (1987).
Phillpotts et al., J. Antimicrobial Chemother. 14, 403-409 (1984).
Kim and Raushel, Biochemistry 27, 7328-7332 (1988) (Sep. 20, 1988).
Stanek et al., The Monosaccharides, Academic Press, 1963, pp. 229-236.
Koreeda et al., J. Org. Chem. 50 (1985), pp. 5912-5913.

Primary Examiner—Johnnie R. Brown
Assistant Examiner—Pamela S. Webber
Attorney, Agent, or Firm—Scott J. Meyer; James W. Williams, Jr.

[57] ABSTRACT

A method is provided for converting therapeutic glycosidase inhibitors to novel prodrugs by phosphorylation of a free hydroxyl group on the molecule to substantially reduce the glycosidase inhibitory activity without thereby substantially reducing the therapeutic activity.

4 Claims, No Drawings

PHOSPHORYLATED GLYCOSIDASE INHIBITOR PRODRUGS

BACKGROUND OF THE INVENTION

This invention relates to and, more particularly, to phosphorylated derivatives of glycosidase inhibitors.

It is known that polyhydroxylated pyrrolidines and piperidines provide an extensive class of powerful and specific glycosidase inhibitors. See, for example, Scofield et al., *Life Sci.* 39, 645-650 (1986); Elbein, *Ann. Rev. Biochem.* 56, 497-534 (1987); and Fleet et.al., *BS Lett.* 237, 128-132 (1988). Several of these *FEBS Lett.* 237, 128-132 (1988). Several of these glycosidase inhibitors have been found to inhibit human immunodeficiency virus (HIV) syncytium formation and virus replication, thereby indicating their potential use as antiretroviral agents. Three such compounds thus suggested as potential anti-AIDS drugs are castanospermine, 1-deoxynojirimycin (DNJ) and 2,5-dihydroxymethyl-3,4-dihydroxypyrrolidine (DMDP). See, for example, Sunkara et.al., *Biochem. Biophys. Res. Commun.* 148(1), 206-210 (1987); Tyms et.al., *Lancet,* Oct. 31, 1987, pp. 1025-1026; Walker et.al., *Proc. Natl. Acad. Sci. USA* 84, 8120-8124 (1987); and Gruters et.al., *Nature* 330, 74-77 (1987). N-alkylated derivatives of these compounds also have been suggested as potential antiviral agents and, in particular, the n-butyl derivative of 1,5-dideoxy-1,5-amino-D-glucitol, also referred to as N-butyl-deoxynojirimycin, has been shown to reduce the virus titer by an order of greater than five logarithms at non-cytotoxic concentrations by Karpas et.al., *Proc. Natl. Acad Sci. USA* 85, 9229-9233 (1988). See, also copending application Ser. No. 07/288,528, filed Dec. 22, 1988, and U.S. Pat. No. 4,849,430.

Some of the glycosidase inhibitors which are potent inhibitors of α-glucosidases, particularly disaccharidases, are suggested as useful agents for treatment of hyperglycemia, hyperlipoproteinaemia, and various gastrointestinal problems. See, e.g., U.S. Pat. Nos. 4,065,562; 4,182,767; 4,278,683; 4,533,668; and 4,639,436.

A problem that arises in the oral administration of the glycosidase inhibitors for therapeutic use is that the concomitant inhibition of the enzymatic splitting of dietary disaccharides can cause undesirable gastrointestinal problems such as diarrhea, digestive flatulance and the like. A means of overcoming these problems without loss of the desired therapeutic benefit of the drug would have significant use.

BRIEF DESCRIPTION OF THE INVENTION

In accordance with the present invention, inhibitors of glycosidase enzymes are converted to novel prodrugs by phosphorylation of a free hydroxyl group on the molecule. As a result, glycosidase inhibition in the gastrointestinal tract is substantially reduced or eliminated upon oral administration of the prodrug. The prodrug is then absorbed in the intestines and metabolized to the active drug by reaction with phosphatase enzymes present in normal tissue and serum, e.g., alkaline phosphatase and glucose-6-phosphatase, which readily remove the labile phosphate group from the prodrug.

The preferred glycosidase inhibitors which are phosphorylated in accordance with the present invention are the polyhydroxylated pyrrolidines and piperidines, especially those illustrated by Fleet et. al., *FEBS Lett.* 237, 128-132 (1988), such as castanospermine, deoxynojirimycin, deoxymannojirimycin and their N-alkylated derivatives, e.g., N-butyl-deoxynojirimycin, and others disclosed in Fleet et.al., copending application Ser. No. 249,144, filed Sept. 26, 1988.

Various of the latter type compounds having a pyranose ring are preferably phosphorylated at the C-6 hydroxyl group. This phosphorylation is conveniently carried out enzymatically by reaction, of the polyhydroxylated piperidine with yeast hexokinase (HK). This enzyme transfers a phosphate group from adenosine triphosphate (ATP) to D-glucose but also is known to phosphorylate D-fructose, D-mannose and D-2-deoxyglucose at almost equivalent rates. The general reaction proceeds as follows:

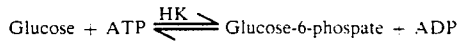

The polyhydroxylated piperidines, e.g. deoxynojirimycin, having a C-6 hydroxyl group are similarly phosphorylated. A typical such enzymic method of preparation of the analogous nojirimycin 6-phosphate is described by Drueckhammer and Wong, *J. Org. Chem.* 50, 5912-5913 (1985.)

The polyhydroxylated piperidines and pyrrolidines can also be chemically phosphorylated. The similarity of the hydroxyl functional groups on these compounds requires selective masking or blocking of several of these hydroxyls so that the desired phosphorylation can be carried out at a specific locus. For example, the selective blocking of a primary hydroxyl group can be carried out by introducing a silyl protecting group at C6 by described by Ogilvie and Hakimelahi, *Carbohydr. Res.* 15; 234-239 (1983). Another convenient blocking group can be introduced to form a ylide such as, for example, by acetonation to form a 2,3-0-isopropylidene derivative of the piperidine. Following phosphorylation of the unprotected hydroxyl groups, the protecting groups can be removed by acid cleavage, for example, by treatment with aqueous trifluoracetic acid. Methods of chemically phosphorylating appropriately blocked polyhydroxylated piperidines and pyrrolidines can be analogous to conventional methods known for preparing sugar phosphates, as described, e.g., by Stanek et.al., *The Monosaccharides,* pp 229-236, Academic Press, New York and London, 1963.

Although methods of making the phosphorylated glycosidase inhibitor prodrugs are described herein, it will be appreciated that these drugs and their method of administration as claimed herein are not limited to any particular method of their preparation.

DETAILED DESCRIPTION OF THE INVENTION

In order to illustrate the invention in greater detail, the invention will be described with particular reference to phosphorylation of the antiviral drug, N-butyl-deoxynojirimycin, to form a useful prodrug. It will be understood that similar prodrugs can be made by analogous phosphorylation of other polyhydroxylated pyrrolidines and piperidines.

N-alkylation of the polyhydroxylated pyrrolidines and piperidines can be conveniently carried out by hydrogenation of the amine together with an appropriate aldehyde in suitable solvent media in the presence of palladium black catalyst as described, e.g., by Fleet et.al. in copending application Ser. No. 249,144, filed Sept. 26, 1988, the disclosure of which is incorporated herein by reference.

In particular, the antiviral drug, N-butyl-deoxynojirimycin, is usually produced by appropriate alkylation of deoxynojirimycin such as by reaction with butyraldehyde. Typical alkylation producers are also described, e.g., in U.S. Pat. Nos. 4,182,767 and 4,639,436. In order to enzymatically phosphorylate this drug it is necessary to first phosphorylate the deoxynojirimycin and then alkylate with the butyraldehyde. The reaction sequence can be illustrated as follows:

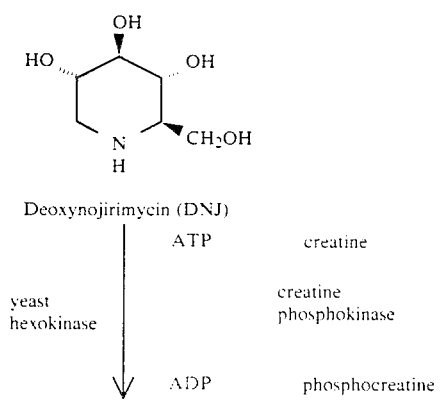

Deoxynojirimycin (DNJ)

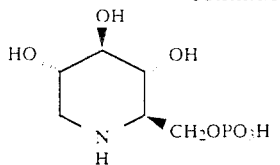

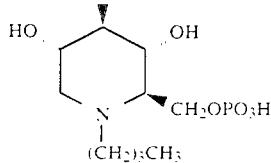

Deoxynojirimycin-6-phosphate chemical alkylation

N-Butyldeoxynojirimycin-6-phosphate

The resulting N-butyl-deoxynojirimycin-6-phosphate can then be administered orally as a prodrug. Although the N-butyl-deoxynojirimycin is a potent inhibitor of a α-phosphorylated derivative is a very weak inhibitor of these enzymes. The reduction of disaccharides enzyme inhibitory activity by converting the N-butyl-deoxynojirimycin to the 6-phosphorylated derivative is illustrated hereinafter in vitro against the procine disaccharidases, sucrase and maltase. Reduction of enzyme inhibitory activity is also illustrated against a cellular-derived procine α-glycosidase.

Upon oral administration of the N-butyl-deoxynojirimycin-6-phosphate, metabolism of the prodrug to the effective antiviral N-butyl-deoxynojirimycin can proceed according to one or more of the following schemes:

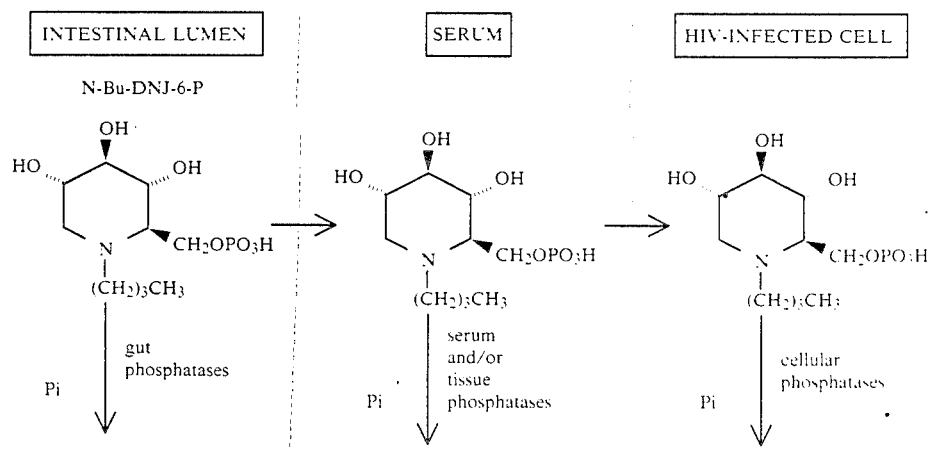

-continued

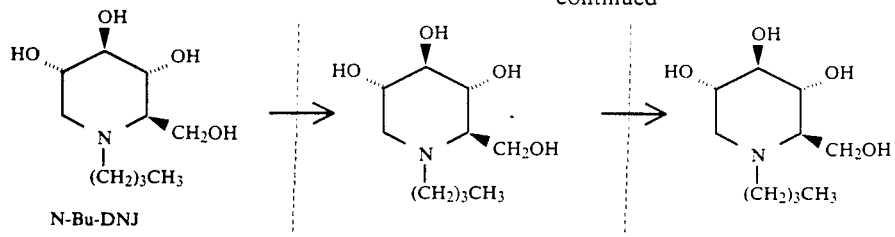

Biolability of the phosphate group of N-butyl-deoxynojirimycin-6-phosphate was demonstrated in vitro by the following reaction in which the compound is completely dephosphorylted.

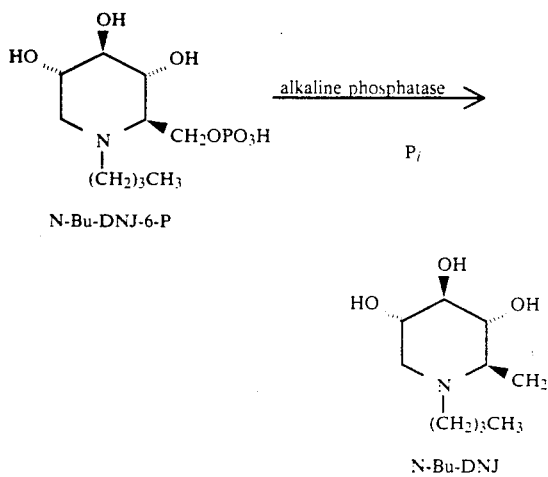

Since alkaline phosphatase exists on the surface of many cells, surface binding of the phosphorylated prodrug to the alkaline phosphatase may be useful for enhancing the targeting of the drug to certain tissues.

The following examples will illustrate the invention in greater detail although it will be appreciated that the invention is not limited to these specific examples.

EXAMPLE 1
SYNTHESIS OF N-BUTYLDEOXYNOJIRIMYCIN-6-PHOSPHATE

The synthesis of N-butyldeoxynojirimycin-6-phosphate (N-BuDNJ-6-P) was achieved by enzymic phosphorylation of the parent compound, deoxynojirimycin (DNJ), and subsequent chemical alkylation of deoxynojirimycin-6-phosphate (DNJ-6-P) by a procedure similar to that used to synthesize N-butyldeoxynojirimycin (N-BuDNJ) from DNJ. It was found necessary to enzymatically phosphorylate DNJ prior to chemical alkylation since N-BuDNJ is not an efficient enzyme substrate.

Synthesis and Isolation of Deoxynojirimycin-6Phosphate. The following are incubated in 50 mM sodium phosphate buffer, pH 8.0, at 30° C.: DNJ, 12 mM; adenosine triphosphate, 30 mM; phosphocreatine, 50 mM; magnesium chloride, 60 mM; 150 units/ml yeast hexokinase (Sigma Type VII) and 20 units/ml bovine heart creatine phosphokinase (Sigma Type III). After 20 h, half the original amount of fresh creatine phosphokinase is added, and incubation continued for a further 20 h. Conversion of DNJ to DNJ-6-P is monitored by high performance anion exchange chromatography, (HPAEC) and typically there is 75% phosphorylation of the substrate, DNJ. Protein is removed by ultrafiltration, and the resulting material subjected to sequential gel-permeation chromatography using a column of TSK-HW40(S) equilibrated and eluted with water and then a similar column equilibrated and eluted with 0.1M sodium acetate buffer, pH 6.0. Purity of the DNJ-6-P is proton NMR spectroscopy.

Alkylation of Deoxynojirimycin-6-phosphate to Give N-Butyldeoxynojirimycin-6-phosphate. The chemical alkylation of DNJ-6-P was analogous to that previously used for the alkylation of DNJ, namely reaction of DNJ-6-P with butyraldehyde in appropriate solvent media under a hydrogen atmosphere in the presence of palladium black catalyst. The resulting product, N-butyldeoxynojirimycin-6-phosphate, was then recovered by chromatographic procedures. The detailed preparation was as follows:

The following were incubated in 0.1M sodium acetate buffer, pH 5.0, at room temperature under an atmosphere of hydrogen: DNJ-6-P, 65 mM; butyraldehyde, 190 mM; and palladium black (catalyst), 20 mg/ml. At the end of the reaction (monitored by high performance anion exchange chromatography), the catalyst was removed by filtration, the products were isolated on a column of CG-400 (OH- form) resin and subsequently recovered by elution with 10% acetic acid. The N-BuDNJ-6-P was purified by chromatography on a column of TSK-HW40(S) equilibrated and eluted with 50 mM sodium acetate buffer, pH 6.0.

EXAMPLE 2
INHIBITION OF α-GLUCOSIDASE I, SUCRASE AND MALTASE BY N-BUYYLFROCYNOJITIMYVIN SNF N-BUTYL-DEOXYNOJIRIMYCIN-6-PHOSPHATE

Inhibition constants were determined for N-BuDNJ and N-BuDNJ-6-P against α-glucosidase I, sucrase and maltase. For comparative purposes similar measurements were made for deoxynojirimycin, deoxynojirimycin-6-phosphate and castanospermine. N-BuDNJ is a potent inhibitor of sucrase and maltase whereas N-BuDNJ-6-P is only a very weak inhibitor of these enzymes and also α-glucosidase I. Methods for the isolation of these enzymes and for determining the inhibition constants are given below.

Porcine Microsomal Alpha-Glucosidase I. Alpha-glucosidase I was isolated from porcine liver microsomes by an affinity chromatographic method similar to that described by Hettkamp et.al., *Eur J. Biochem.* 142, 85–90 (1981). The purified preparation had a specific activity of 10000 units/mg protein as assayed against [$^{14}$C-Glc]Glc$_3$Man$_9$GlcNAc$_2$, a biosynthetically-labelled substrate isolated from porcine thyroid microsomes.

Inhibition constants for the various DNJ derivatives and castanospermine were determined assuming competitive inhibition and were derived from the initial rates for the hydrolysis of $[^{14}C\text{-Glc}]Glc_3Man_9GlcNAc_2$ (at a concentration of 0.044 μM), at pH7.0 and 37° C. in the presence and absence of several fixed concentrations of each inhibitor.

Porcine Intestinal Sucrase and Maltase. A sucrase-isomaltase complex was extracted from pig small intestine by treatment with urea and then solubilized by digestion with papain. The enzyme-complex was recovered by ethanol precipitation and then further purified by cellulose DE-52 anion exchange chromatography. The activity of sucrase was assayed by incubating an appropriate amount of enzyme at 37° C. in a final volume of 150 μl containing 25 mM sodium citrate buffer, pH 6.0, and 30 mM sucrose as substrate. After 30 min. the enzyme was inactivated by heating at 100° C. for 3 min, the reaction mixture centrifuged at 15000×g for 15 min and a 50 μl aliquot of the supernatant removed and the enzymereleased glucose determined by the glucose oxidase-peroxidase method described by Trinder, Ann. Clin. Biochem. 6, 24 (1969). Under the standard assay conditions, the release of glucose was linear up to 10% hydrolysis of the substrate. The purified enzyme preparation had a specific activity of 4.08 units sucrase/mg protein. Maltase activity associated with the sucrase-isomaltase complex [Kolinska and Semenze, Biochim. Biophys. Acta 146, 181 (1967)] was assayed in a manner similar to sucrase except that the substrate was 30 mM maltose. Under the standard assay conditions release of glucose was linear up to 8% hydrolysis of the substrate. The specific activity of maltase was 15.2 units/mg protein.

Inhibition constants for the various DNJ derivatives and castanospermine were determined from Lineweaver-Burk plots of the enzyme-catalyzed reaction in the presence and absence of different fixed concentrations of each inhibitor. Incubations using sucrase were for 30 min at a concentration of 90 milliunits/ml and for maltase were for 12 min at a concentration of 80 milliunits/ml.

TABLE I

Activity of Amino-sugar Derivatives Against Porcine Glucosidase I, Sucrase and Maltase

| Compound | $K_i$ (μM) | | |
|---|---|---|---|
| | Microsomal α-Glucosidase I | Intestinal Sucrase | Intestinal Maltase |
| Castanospermine | 0.04 | *0.064 | 0.34 |
| N-BuDNJ | 0.22 | 0.18 | 0.92 |
| N-BuDNJ-6-P | 4000 | 1500 | 330 |
| DNJ | 0.83 | 0.050 | 0.09 |
| DNJ-6-P | 6600 | 520 | 1.0 |

*Non-competitive inhibitor, no pre-incubation

EXAMPLE 3

N-Butyldeoxynojirimycin-6-phosphate (1 mM) was incubated with bovine intestinal alkaline phosphatase (Sigma Type VII, 130 U/ml) at 37° C. n 0.1 m $Na_2$-$CO_3$/$NaHCO_3$ buffer, pH 9.5. After incubation for 16 h the reaction products were assayed by high performance anion exchange chromatography which established that the N-butyldeoxynojirimycin-6-phosphate had been completely dephosphorylated.

The prodrug antiviral agents described herein can be used for administration to patients infected with the viruses by conventional means, preferably in formulations with pharmaceutically acceptable diluents and carriers. These agents can be used in the free amine form or in the salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human dosage would normally range upward from about one milligram of the prodrug. A suitable route of administration is orally in the form of capsules, tablets, syrups, elixirs and the like, although parenteral administration also can be used. Appropriate formulations of the prodrug in pharmaceutically acceptable diluents and carriers in therapeutic dosage form can be prepared by reference to general texts in the field such as, for example, *Remington's Pharmaceutical Sciences*, Ed. Arthur Osol, 16th ed., 1980, Mack Publishing Co., Easton, PA.

Various other examples will be apparent to the person skilled in the art after reading the present disclosure without departing from the spirit and scope of the invention. It is intended that all such examples be included within the scope of the appended claims.

We claim:

1. A method of substantially reducing the glycosidase inhibitory activity against intestinal disaccharidases of a therapeutic 1-deoxynyjirimycin-based glycosidase inhibitor having a free hydroxy group on the molecule at C-6 without thereby substantially reducing its potential therapeutic activity which consists in converting said glycosidase inhibitor to a 6-phosphorylated derivative which is amenable upon oral administration to dephosphorylation by normal tissue or serum phosphatases.

2. A method of substantially reducing the glycosidase inhibitory activity against intestinal disaccharidases of a therapeutic 1-deoxynojirimycin-based glycosidase inhibitor having a free hydroxy group on the molecule at C-6 without thereby substantially reducing its potential therapeutic activity which consists in converting said glycosidase inhibitor by reaction with hexokinase to a 6-phosphorylated derivative which is amenable upon oral administration to dephosphorylation by normal tissue or serum phosphatases.

3. The method of claim 2, in which the glycosidase inhibitor is N-butyl-deoxynojirimycin.

4. The method of claim 2, in which the 6-phosphorylated derivative is N-butyl-deoxynojirimycin-6-phosphate.

* * * * *

UNITED STATES PATENT AND TRADEMARK OFFICE
CERTIFICATE OF CORRECTION

PATENT NO. : 5,043,273

DATED : August 27, 1991

INVENTOR(S) : Peter R. Scudder, Raymond A. Dwek, Thomas W. Rademacher and Gary S. Jacob It is certified that error appears in the above-identified patent and that said Letters Patent is hereby corrected as shown below:

At col. 1, line 6, after "relates to" insert --novel prodrugs--.
At col. 1, lines 12-13, delete "BS Lett. 237, 128-132 (1988). Several of these". Col. 2, line 35, after "by" (first occurrence) insert --reaction with t-butyldimethylsilyl chloride as--. Col. 3, line 13, insert --PROTOCOL FOR THE SYNTHESIS OF N-BUTYLDEOXYNOJIRIMYCIN-6-PHOSPHATE--.
At col. 3, lines 22-28, the terms "ATP" and "ADP" should be connected by two semi-circular arrows that form a circle, and the terms "creatine" and "phosphocreatine" should be connected by a single semi-circular arrow that at its center point abuts said circle and that points to creatine. At col. 4, lines 28-29, cancel "a α-phosphorylated" and insert --α-glucosidase 1 and gut disaccharidases, the 6-phosphorylated--.
At col. 4, lines 33 & 36, "procine" should read --porcine--. At col. 6, line 38, after "column of" insert --Amberlite® --. At col. 6, line 47, "N-BUYYLFROCYNOJITIMYVIN SNF" should read --N-BUTYLDEOXYNOJIRIMYCIN AND--.
At col. 7, line 60, "m" should read --M--.

Signed and Sealed this

Twenty-fourth Day of August, 1993

Attest:

BRUCE LEHMAN

Attesting Officer    Commissioner of Patents and Trademarks